United States Patent
Razzaqi (10) Patent No.: US 11,255,856 B2
(45) Date of Patent: Feb. 22, 2022

(54) IMMUNOASSAY FOR DETECTING TUMOR PYRUVATE KINASE M2

(71) Applicant: Mahboubeh Razzaqi, Qom (IR)

(72) Inventor: Mahboubeh Razzaqi, Qom (IR)

(73) Assignee: TARBIAT MODARES UNIVERSITY, Tehran (IR)

( * ) Notice: Subject to any disclaimer, the term of this patent is extended or adjusted under 35 U.S.C. 154(b) by 21 days.

(21) Appl. No.: 16/935,833

(22) Filed: Jul. 22, 2020

(65) Prior Publication Data

US 2021/0140966 A1     May 13, 2021

Related U.S. Application Data

(60) Provisional application No. 62/878,081, filed on Jul. 24, 2019.

(51) Int. Cl.
*G01N 33/573* (2006.01)
*G01N 33/577* (2006.01)
*C07K 16/40* (2006.01)
*G01N 33/558* (2006.01)

(52) U.S. Cl.
CPC ......... *G01N 33/573* (2013.01); *G01N 33/577* (2013.01); *C07K 16/40* (2013.01); *C07K 2317/34* (2013.01); *G01N 33/558* (2013.01)

(58) Field of Classification Search
CPC ........ C07K 16/18; C07K 16/30; C07K 16/40; C07K 2317/34; C07K 2317/56; C07K 2317/565; G01N 33/573; G01N 33/577; G01N 33/58; G01N 33/558; G01N 33/543; G01N 33/54306
See application file for complete search history.

(56) References Cited

U.S. PATENT DOCUMENTS 5,972,628 A * 10/1999 Eigenbrodt ............ C07K 16/40
                                                 435/330
2008/0153119 A1* 6/2008 Scheefers-Borchel ......................
                                         G01N 33/57446
                                                 435/15

FOREIGN PATENT DOCUMENTS

CN        106405094 B * 3/2018
WO     WO-2006055880 A2 * 5/2006 ....... G01N 33/57449

OTHER PUBLICATIONS

Razzaqi M et al. A critical challenge in the development of antibody: Selecting the appropriate fragment of the target protein as an antigen based on various epitopes or similar structure. Mol Immunol. 2019, 111, 128-135. Available online May 1, 2019. (Year: 2019).*
Translation of CN106405094B by Google Patents, retrieved from internet on Sep. 28, 2021. (Year: 2021).*

* cited by examiner

*Primary Examiner* — Kimberly Ballard
(74) *Attorney, Agent, or Firm* — Bajwa IP Law Firm; Haris Zaheer Bajwa (57) ABSTRACT

An immunoassay kit including a monoclonal antibody coupled to a labeling agent (labeled mAb) for detecting tumor pyruvate kinase M2 (tM2-PK) in a biological sample. The monoclonal antibody includes a heavy chain variable region (HCVR) including heavy chain complementarity-determining regions (CDRs) (SEQ ID NOs: 3, 4, and 5) and a light chain variable region (LCVR) including light CDRs (SEQ ID NOs: 7, 8, and 9).

20 Claims, 5 Drawing Sheets
Specification includes a Sequence Listing.

IMMUNOASSAY FOR DETECTING TUMOR PYRUVATE KINASE M2

CROSS-REFERENCE TO RELATED APPLICATION

This application claims the benefit of priority from U.S. Provisional Patent Application Ser. No. 62/878,081, filed on Jul. 24, 2019, and entitled "Development of rapid lateral flow test for tumor Pyruvate Kinase M2 (PKM2) detection using gold nanoparticle for the purpose of colorectal cancer screening," which is incorporated herein by reference in its entirety.

TECHNICAL FIELD

The present disclosure generally relates to cancer diagnosis, particularly to immunoassays for detecting tumor-specific biomarkers, and more particularly, to an immunoassay kit for detecting tumor pyruvate kinase M2 in a biological sample.

BACKGROUND

Colorectal cancer (CRC) is the third most common cancer and the second leading cause of cancer deaths in the world. Since colorectal cancer tends to grow slowly for a long time without any clinical symptoms, screening is the best approach for early detection of precursors such as precancerous polyps which may completely prevent the consequences of colorectal cancer. However, the early diagnosis of colorectal cancer remains a challenge and about half of patients with colorectal cancer diagnosed at the late stages. Currently, there are several common screening methods for the early diagnosis of colorectal cancer, such as colonoscopy and fecal occult blood test (FOBT). The FOBT screening such as guaiac-based FOBT (gFOBT) and immunochemical FOBT (iFOBT) examine the presence of blood in the fecal sample.

Although colonoscopy is a diagnostic gold standard for CRC, its acceptance in society is low due to invasiveness and high cost even in developed countries. On the other hand, the gFOBT requires special dietary and drug restriction several days before conducting the test which makes the gFOBT unpleasant for the public. Also, high false-positive results, detecting only bleeding tumors, and low sensitivity for precancerous polyps, reduces the accuracy of the gFOBT test. In order to overcome the problems of the gFOBT test for CRC detection, immunochemical FOBT (iFOBT) or fecal immunochemical test (FIT) have been developed which detect human hemoglobin in a fecal sample with better sensitivity than gFOBT and without any restriction. However, an FIT screening still has a low sensitivity for precancerous polyps and non-bleeding tumors.

Another strategy for cancer screening and early detection of tumors is detecting tumor-specific markers in biological samples of patients by conducting different immunoassays. Tumor pyruvate kinase M2 (tM2-PK) is overexpressed in colorectal tumor cells and considered as a sensitive, specific, reliable, and effective colorectal cancer biomarker which has an acceptable application prospect in early diagnosis and prognosis judgment of malignant tumors. Hence, there is a need for a non-invasive, low cost, and simple CRC screening immunoassay and an immunoassay kit for early detection of precancerous polyps, bleeding tumors, and non-bleeding tumors with high sensitivity and specificity.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary immunoassay kit for detecting tumor pyruvate kinase M2 (tM2-PK) in a biological sample. In an exemplary embodiment, the immunoassay kit may include a monoclonal antibody coupled to a labeling agent (a labeled mAb). In an exemplary embodiment, the monoclonal antibody may include a heavy chain variable region (HCVR) and a light chain variable region (LCVR). In an exemplary embodiment, the HCVR may include heavy chain complementarity-determining regions (CDRs) including SEQ ID NOs: 3, 4, and 5. In an exemplary embodiment, the LCVR may include light chain CDRs including SEQ ID NOs: 7, 8, and 9.

In an exemplary embodiment, the HCVR may have an amino acid sequence of SEQ ID NO: 6. In an exemplary embodiment, the LCVR may have an amino acid sequence of SEQ ID NO: 10. In an exemplary embodiment, the exemplary immunoassay kit may further include a polyclonal antibody being capable of binding to an epitope within amino acids 433 to 503 of the tM2-PK (SEQ ID NO: 2). In an exemplary embodiment, the monoclonal antibody may have an isotype of immunoglobulin M (IgM). In an exemplary embodiment, the labeling agent may include at least one of a luminescent particle, a quantum dot, a chromogen, a catalyst, and a radioactive compound.

In an exemplary embodiment, the immunoassay kit may further include a conjugate pad containing the monoclonal antibody coupled to the labeling agent (the labeled mAb), a nitrocellulose membrane, and an absorbent pad located downstream of the nitrocellulose membrane. In an exemplary embodiment, the conjugate pad may include the monoclonal antibody coupled to the labeling agent (the labeled mAb). In an exemplary embodiment, the nitrocellulose membrane may include a test zone located downstream of the conjugate pad and a control zone located downstream of the test zone. In an exemplary embodiment, the monoclonal antibody may be configured to bind to a first portion of the tM2-PK.

In an exemplary embodiment, the test zone may include a first immobilized capture reagent configured to bind to at a second portion of the tM2-PK. In an exemplary embodiment, the second portion of the tM2-PK may include one or more portions of the tM2-PK other than the first portion of the tM2-PK. In an exemplary embodiment, the control zone may include a second immobilized capture reagent configured to bind to the monoclonal antibody. In an exemplary embodiment, the absorbent pad may be configured to promote a capillary flow of the biological sample from the conjugate pad toward the control zone.

In an exemplary embodiment, the first immobilized capture reagent may include at least one of a polyclonal antibody, a monoclonal antibody, an antibody fragment, an aptamer. In an exemplary embodiment, the first immobilized capture reagent may include the polyclonal antibody being capable of binding to an epitope within amino acids 433 to 503 of the tM2-PK (SEQ ID NO: 2). In an exemplary embodiment, the second immobilized capture reagent may include at least one of an antibody, an antibody fragment, and an aptamer. In an exemplary embodiment, the immunoassay kit has a cutoff value of 4 U/ml of the tM2-PK in the biological sample for detecting the tM2-PK in the biological sample.

In another general aspect, the present disclosure describes an exemplary immunoassay for detecting tumor pyruvate kinase M2 (tM2-PK) in the biological sample. In an exemplary embodiment, the immunoassay may include putting the biological sample in contact with a monoclonal antibody coupled to a labeling agent (a labeled mAb) and detecting the presence of the tM2-PK in the biological sample responsive to detecting formation of a complex between the tM2-PK and the labeled mAb. In an exemplary embodiment, the monoclonal may include a heavy chain variable region (HCVR) including heavy chain complementarity-determining regions (CDRs) (SEQ ID NOs: 3, 4, and 5) and a light chain variable region (LCVR) including light chain CDRs (SEQ ID NOs: 7, 8, and 9).

In an exemplary embodiment, detecting the presence of the tM2-PK in the biological sample may include detecting the presence of the tM2-PK in the biological sample with a cutoff value of about 4 U/ml of the tM2-PK in the biological sample. In an exemplary embodiment, detecting the presence of the tM2-PK in the biological sample may include detecting the presence of the tM2-PK in the biological sample by conducting at least one of a chemiluminescent assay, an immunofluorescent assay, enzyme-linked immunosorbent assay (ELISA), radioimmunoassay, a Western blot assay, an enzyme immunoassay, an immunoprecipitation assay, an immunohistochemical assay, an immunochromatographic assay, a dot blot assay, a slot blot assay.

In an exemplary embodiment, detecting the presence of the tM2-PK in the biological sample may include detecting the presence of the tM2-PK in the biological sample by conducting a lateral flow assay (LFA). In an exemplary embodiment, conducting the lateral flow assay (LFA) may include providing a lateral flow assay (LFA) kit. In an exemplary embodiment, the LFA kit may include a conjugate pad containing the monoclonal antibody coupled to the labeling agent (the labeled mAb), a nitrocellulose membrane, and an absorbent pad located downstream of the nitrocellulose membrane. In an exemplary embodiment, the monoclonal antibody may be configured to bind to a first portion of the tM2-PK. In an exemplary embodiment, the control zone may include a second immobilized capture reagent configured to bind to the monoclonal antibody. In an exemplary embodiment, the absorbent pad may be configured to promote a capillary flow of the biological sample from the conjugate pad toward the control zone.

In an exemplary embodiment, the nitrocellulose membrane may include a test zone located downstream of the conjugate pad and a control zone located downstream of the test zone. In an exemplary embodiment, the test zone may include a first immobilized capture reagent configured to bind to a second portion of the tM2-PK. In an exemplary embodiment, the second portion of the tM2-PK may include one or more portions of the tM2-PK other than the first portion of the tM2-PK.

Other exemplary systems, methods, features, and advantages of the implementations will be or will become, apparent to one of ordinary skill in the art upon examination of the following figures and detailed description. It is intended that all such additional systems, methods, features, and advantages be included within this description and this summary, be within the scope of the implementations and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

The present disclosure describes an exemplary immunoassay and an exemplary immunoassay kit including an exemplary monoclonal antibody against tumor pyruvate kinase M2 (tM2-PK) for detecting tM2-PK in a biological sample, such as feces and blood. The exemplary monoclonal antibody specifically binds tM2-PK and does not cross-react with any other pyruvate kinase isoenzymes. In the present disclosure "tM2-PK" refers to tumor pyruvate kinase M2 which is overexpressed in tumor cells in a dimeric form and is different from a tetrameric form of the pyruvate kinase M2 which may be found in embryonic cells and stem cells. In the present disclosure, "overexpressed" refers to be produced in abnormally large amounts.

The exemplary immunoassay kit may be used for non-invasive colorectal cancer (CRC) screening by detecting precancerous polyps, non-bleeding tumors, and bleeding tumors, with high sensitivity and high specificity without any dietary restriction. Since the exemplary immunoassay may not rely on presence of blood in the biological samples, the exemplary immunoassay may not provide false-positive results due to other common bleeding diseases such as hemorrhoids and fissures. As a result, the exemplary immunoassay kit may have higher accuracy than a conventional fecal immunochemical test (FIT) and may be used as a suitable candidate for colorectal cancer screening.

Figure 1:
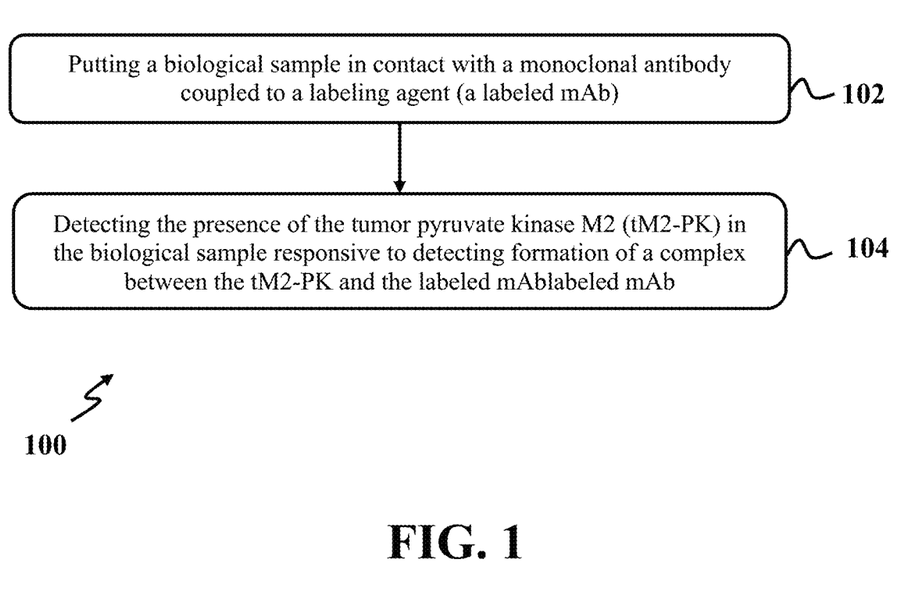
FIG. 1 illustrates a flowchart of an exemplary immunoassay for detecting tumor pyruvate kinase M2 (tM2-PK) in a biological sample, consistent with one or more exemplary embodiments of the present disclosure.

FIG. 1A shows a flowchart of an exemplary immunoassay 100 for detecting tumor pyruvate kinase M2 (tM2-PK) in a biological sample, consistent with one or more exemplary embodiments of the present disclosure. An exemplary immunoassay 100 may include putting the biological sample in contact with a monoclonal antibody coupled to a labeling agent (a labeled mAb) (step 102) and detecting the presence of the tM2-PK in the biological sample responsive to detecting formation of a complex between the tM2-PK and the labeled mAb (step 104). In an exemplary embodiment, immunoassay 100 for detecting the tM2-PK in the biological sample may be implemented using an exemplary immunoassay kit. In the present disclosure, "a monoclonal antibody coupled to a labeling agent" may be abbreviated as a labeled mAb.

In further detail with respect to step 102, in an exemplary embodiment, putting the biological sample in contact with a labeled mAb may include forming antigen-antibody complexes between the labeled mAb and the tM2-PK. In an exemplary embodiment, forming the antigen-antibody complexes between the labeled mAb and the tM2-PK may include forming the antigen-antibody complexes between the labeled mAb and the tM2-PK if the tM2-PK is present in the biological sample. In an exemplary embodiment, the biological sample may include a fecal sample or a blood sample. In the present disclosure, "fecal sample" may refer to a sample containing feces dissolved in an extraction buffer.

In an exemplary embodiment, the monoclonal antibody may be configured to bind to a first portion of the tM2-PK. In an exemplary embodiment, the first portion of the tM2-PK may include an epitope within amino acids 393 to 428 (SEQ ID NO: 2) of the tM2-PK (SEQ ID NO: 11). In an exemplary embodiment, the monoclonal antibody may not cross-react with other pyruvate kinase isoenzymes. In an exemplary embodiment, the monoclonal antibody may have an isotype of immunoglobulin M (IgM) with more avidity than immunoglobulin G (IgG).

In an exemplary embodiment, the monoclonal may include a heavy chain variable region (HCVR) and a light chain variable region (LCVR). In an exemplary embodiment, the HCVR may include heavy chain complementarity-determining regions (CDRs) of SEQ ID NOs: 3, 4, and 5. In an exemplary embodiment, the LCVR may include light chain CDRs of SEQ ID NOs: 7, 8, and 9. In an exemplary embodiment, the HCVR may include SEQ ID NO: 6. In an exemplary embodiment, the LCVR may include SEQ ID NO: 10.

In an exemplary embodiment, the monoclonal antibody may include at least one of a mouse antibody, a chimeric antibody, a humanized antibody, a human antibody. In an exemplary embodiment, the monoclonal antibody may be produced using a recombinant protein technology or a hybridoma technology. In an exemplary embodiment, the labeling agent may include at least one of a luminescent particle, a quantum dot, a chromogen, a catalyst, and a radioactive compound. In an exemplary embodiment, the labeling agent may include gold (Au) nanoparticles.

In further detail with respect to step 104, in an exemplary embodiment, detecting the presence of the tM2-PK in the biological sample may include detecting the presence of the tM2-PK in the biological sample responsive to detecting formation of a complex between the tM2-PK and the labeled mAb. In an exemplary embodiment, detecting formation of the complex between the tM2-PK and the labeled mAb may include detecting the complex between the tM2-PK and the labeled mAb by conducting at least one of a chemiluminescent assay, an immunofluorescent assay, enzyme-linked immunosorbent assay (ELISA), radioimmunoassay, a Western blot assay, an enzyme immunoassay, an immunoprecipitation assay, an immunohistochemical assay, an immunochromatographic assay, a dot blot assay, a slot blot assay.

In an exemplary embodiment, the complex between the tM2-PK and the labeled mAb may include a gold-labeled mAb-tM2-PK complex. In an exemplary embodiment, detecting the presence of the tM2-PK in the biological sample may include detecting the presence of the tM2-PK in the biological sample with a cutoff value of 4 U/ml of the tM2-PK in a fecal sample. In an exemplary embodiment, detecting the presence of the tM2-PK in the biological sample may include detecting the presence of the tM2-PK in the biological sample with a cutoff value of 15 U/ml of the tM2-PK in a blood sample. It should be noted that presence of the tM2-PK with a concentration less than 4 U/ml in a fecal sample and less than 15 U/ml in a blood sample is considered as a normal range for healthy subjects.

In an exemplary embodiment, immunoassay 100 for detecting the tM2-PK in the biological sample may be implemented using an immunoassay kit containing the labeled mAb. In an exemplary embodiment, the immunoassay kit may further include a polyclonal antibody for capturing complexes including tM2-PK and -gold labeled-mAb. In an exemplary embodiment, the polyclonal antibody may bind to an epitope within amino acids 433 to 503 of the tM2-PK (SEQ ID NO: 2).

Figure 2:
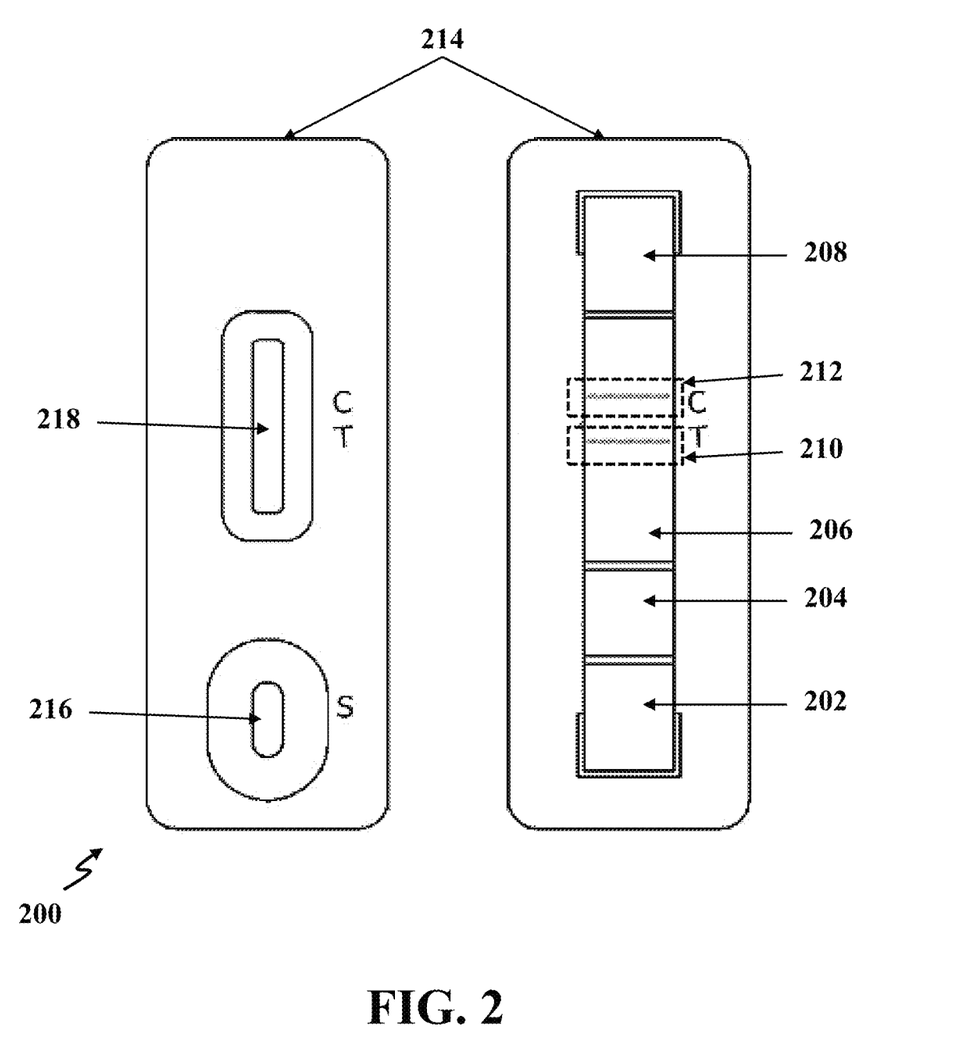
FIG. 2 illustrates a schematic representation of a lateral flow assay kit as an exemplary immunoassay kit for detecting PKM2 in a biological sample, consistent with one or more exemplary embodiments of the present disclosure.

In an exemplary embodiment, detecting the presence of the tM2-PK in the biological sample comprises detecting the presence of the tM2-PK in the biological sample by conducting a lateral flow assay (LFA). In an exemplary embodiment, conducting the lateral flow assay (LFA) may include providing a lateral flow assay (LFA) kit. FIG. 2 illustrates a schematic representation of a lateral flow assay kit 200 as an exemplary immunoassay kit for detecting tumor pyruvate kinase M2 (tM2-PK) in a biological sample, consistent with one or more exemplary embodiments of the present disclosure.

Referring to FIG. 2, in an exemplary embodiment, the LFA kit may include a sample pad 202, a conjugate pad 204, a nitrocellulose membrane 206, and an absorbent pad 208, a cassette 214, a sample port 216, and a result window 218. In an exemplary embodiment, conjugate pad 204 may include a monoclonal antibody coupled to a labeling agent (a labeled mAb). In the present disclosure, "coupled to a labeling agent" refers to being labeled with a labeling agent through binding to a labeling agent. In an exemplary embodiment, the monoclonal antibody is configured to bind to a first portion of the tM2-PK. In an exemplary embodiment, nitrocellulose membrane 206 may include a test zone 210 located downstream of conjugate pad 204, and a control zone 212 located downstream of test zone 210. In an exemplary embodiment, absorbent pad 208 may be located downstream of the nitrocellulose membrane 206. In an exemplary embodiment, absorbent pad 208 may be configured to promote a capillary flow of the biological sample from conjugate pad 204 toward control zone 212.

In an exemplary embodiment, test zone 210 may include a first immobilized capture reagent. In the present disclosure, "first immobilized capture reagent" may refer to a capture reagent which is fixed and may be capable of binding to a second portion of the tM2-PK. In an exemplary embodiment, the first immobilized capture reagent may be configured to bind to a second portion of the tM2-PK. In an exemplary embodiment, the second portion may include one or more portions of the tM2-PK other than the first portion of the tM2-PK. In an exemplary embodiment, the first immobilized capture reagent may include at least one of a polyclonal antibody, a monoclonal antibody, an antibody fragment, an aptamer. In an exemplary embodiment, the first immobilized capture reagent may include the polyclonal antibody being capable of binding to an epitope within amino acids 433 to 503 of the tM2-PK (SEQ ID NO: 2). In an exemplary embodiment, the first immobilized capture reagent may include at least one of a rabbit polyclonal antibody, a monkey polyclonal antibody, and a goat polyclonal antibody.

In an exemplary embodiment, control zone 212 may include a second immobilized capture reagent. In the present disclosure, "second immobilized capture reagent" may refer to a capture reagent which is fixed and may be capable of binding to the monoclonal antibody. In an exemplary embodiment, the second immobilized capture reagent may be configured to bind to the monoclonal antibody. In an exemplary embodiment, the second immobilized capture reagent may bind to the fragment crystallizable (Fc) region of the monoclonal antibody. In an exemplary embodiment, the second immobilized capture reagent may include at least one of an antibody, an antibody fragment, and an aptamer.

In an exemplary embodiment, an exemplary immunoassay kit may be used for detecting precancerous polyps, non-bleeding tumors and bleeding tumors of colorectal cancer (CRC) without size limitation with a specificity of about 91.4% and a sensitivity of about 80% for precancerous polyps and about 100% for colorectal cancer. As a result, an exemplary immunoassay kit may be used in screening programs of colorectal cancer.

In an exemplary embodiment, LFA kit 200 may be used for detecting precancerous polyps, non-bleeding tumors and bleeding tumors of colorectal cancer (CRC) by applying a small amount of a fecal sample into sample port 216 without any need for equipment or requiring any training people for reading the results. In an exemplary embodiment, detecting CRC using exemplary LFA kit 200 may be easy, fast, cost-effective, and non-invasive which may increase public acceptance of the test using LFA kit 200 in comparison with a colonoscopy. In an exemplary embodiment, results of LFA kit 200 may be visible to a naked eye in the result window 218 in a time period between about 10 minutes and about 15 minutes. Accordingly, in an exemplary embodiment, quick results may be provided.

EXAMPLES

Example 1: Production of the Monoclonal Antibody and Polyclonal Antibody Against the Tumor Pyruvate Kinase M2 (tM2-PK)

It is often not possible to use a native protein as an antigen for antibody development due to being expensive. Although the use of recombinant full-length protein as an antigen has a high probability to produce antibodies that may be able to detect native proteins, the production of a full-length protein incorporates many challenges in the expression and purification processes of the recombinant full-length protein due to large size of the recombinant full-length protein, such as protein inactivity and inclusion body (IB) formation. Furthermore, since antibodies are produced against different epitopes of the antigen, it is more likely that some antibodies have non-specific reactions with different homolog epitopes in other proteins which results in a nonspecific cross-reaction. As a result, using truncated fragments of a protein with no homology with other proteins as an antigen is a popular strategy for developing specific antibodies with minimized cross-reactivity. In an exemplary embodiment, truncated fragments of a protein may refer to parts of a native protein exclusively present in the native protein without homology with other proteins. In an exemplary embodiment, truncated fragments of a protein may be produced separately.

In this example, two truncated fragments (SEQ ID NO: 1 and SEQ ID NO: 2) of the tM2-PK were selected for antibody production as follows. In order to select the truncated fragments (SEQ ID NO: 1 and SEQ ID NO: 2), the amino acid sequence of the tM2-PK was analyzed and epitope regions of the tM2-PK were predicted using in-silico studies. Also, homologous parts of the epitope regions were not considered during selecting the truncated fragment; therefore, using selected truncated fragments may lead to producing antibodies with minimized cross-reactivity. After choosing the truncated fragments, recombinant truncated fragments were expressed in *E. coli* (strain B/BL21-DE3) with a His-tag at the C terminal of the amino acid sequence of the truncated fragments. The optimum expression of the truncated fragments was obtained by adding 0.1 mM isopropyl β-d-1-thiogalactopyranoside (IPTG) to a culture medium of the *E. coli* and incubating at a temperature of about 18° C. for a time period of about for 18 hours. The soluble fractions of the expressed truncated fragments were purified using a nickel-nitrilotriacetic acid Ni-NTA column. In the present disclosure, "expression" refers to a way in which proteins are synthesized, modified and regulated in living organisms.

Figure 3A:
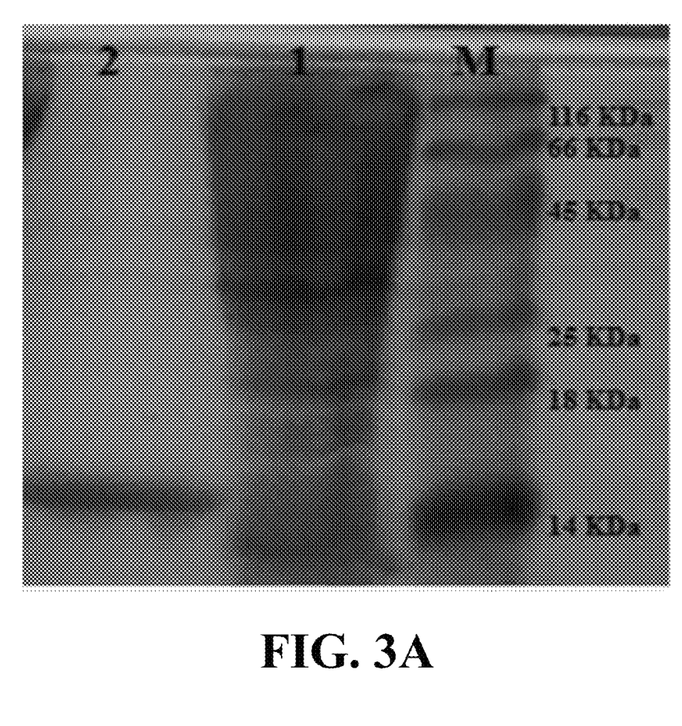
FIG. 3A illustrates a sodium dodecyl sulfate-polyacrylamide gel electrophoresis (SDS-PAGE) profile of a truncated fragment (SEQ ID NO: 1) of the tM2-PK used for a producing a monoclonal antibody against the tM2-PK, consistent with one or more exemplary embodiments of the present disclosure.

FIG. 3A illustrates a sodium dodecyl sulfate-polyacrylamide gel electrophoresis (SDS-PAGE) profile of a truncated fragment (SEQ ID NO: 1) of the tM2-PK used for a producing a monoclonal antibody against the tM2-PK, consistent with one or more exemplary embodiments of the present disclosure. Lane M is related to a molecular weight marker, lane 1 is for the flow-through, and lane 2 is corresponding to the purified truncated fragment. Referring to FIG. 3A, the truncated fragment (SEQ ID NO: 1) has a molecular weight of about 14 kDa.

Figure 3B:
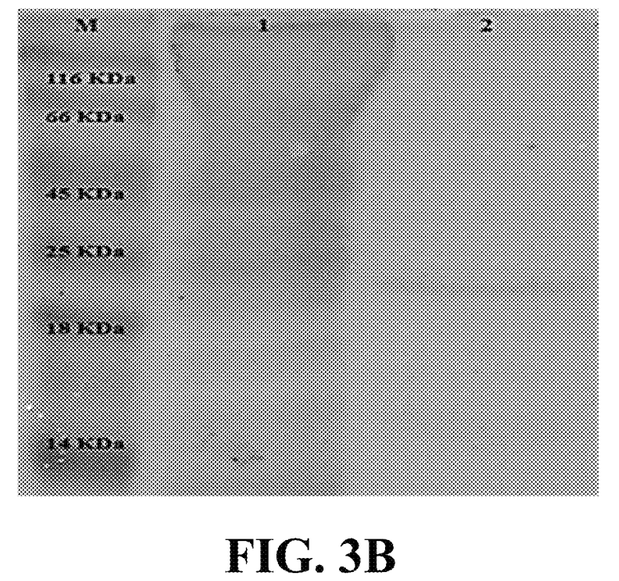
FIG. 3B illustrates a sodium dodecyl sulfate-polyacrylamide gel electrophoresis (SDS-PAGE) profile of a truncated fragment (SEQ ID NO: 2) of the tM2-PK used for a producing a polyclonal antibody against the tM2-PK, consistent with one or more exemplary embodiments of the present disclosure.

FIG. 3B illustrates a sodium dodecyl sulfate-polyacrylamide gel electrophoresis (SDS-PAGE) profile of a truncated fragment (SEQ ID NO: 2) of the tM2-PK used for a producing a polyclonal antibody against the tM2-PK, consistent with one or more exemplary embodiments of the present disclosure. Lane M is related to a molecular weight marker, lane 1 is for the flow-through, and lane 2 is corresponding to the purified truncated fragment. Referring to FIG. 3B, the truncated fragment (SEQ ID NO: 2) has a molecular weight of about 25 kDa.

Rodents and rabbits are often used to produce antibodies for a variety of research objectives, such as polyclonal and monoclonal antibody production. In this example, mice and rabbits were immunized using the truncated fragments of tM2-PK for producing monoclonal and polyclonal antibodies against the tM2-PK. Due to the fact that, antibodies produced in mice and rabbits are similar to the human antibodies, the monoclonal antibody produced in mice and the polyclonal antibody produced in rabbit may be used for capturing tumor PKM2 in biological samples of human.

In the next step, the monoclonal antibody against the tM2-PK was produced using hybridoma technology. Firstly, BALB/c female mice (6-8 weeks old) were immunized using the purified truncated fragment (SEQ ID NO: 1) and spleen cells of the immunized mice were obtained. After that, monoclonal hybridoma cell lines were produced by fusing spleen cells of the immunized mice with the SP2/0 myeloma cell line. Then, a monoclonal hybridoma cell line named with C15 was selected and confirmed to produce the monoclonal antibody (mAb) specific to the tM2-PK, which does not cross-react with other types of PKM2. The monoclonal has a heavy chain variable region (HCVR) (SEQ ID NO: 6) and a light chain variable region (LCVR) (SEQ ID NO: 10).

In the next step, the hybridoma cells were expanded in the RPMI medium containing 10% FBS and intraperitoneally injected into the BALB/c mice that had been pretreated with an intraperitoneal injection of pristine with an amount of about 0.5 mL. In the end, ascites fluid was taken from the mice and the mAb was purified based on IgM isotype due to higher avidity than an IgG isotype. Also, the polyclonal antibody against the tM2-PK was produced by immunizing two female rabbits with a weight between about 1.5 Kg and about 2 Kg with the purified truncated fragment (SEQ ID NO: 2) and the produced polyclonal antibody was purified from the immunized serum of the rabbits.

Example 2: Production of the Lateral Flow Assay Kit for Detecting the Tumor Pyruvate Kinase M2 (tM2-PK) in a Fecal Sample Immunochromatographic rapid tests such as the lateral flow assay (LFA) is an appropriate candidate for performing colorectal cancer screening everywhere without any need for laboratory facilities. Also, low cost, ease of use, and quick results visible to a naked eye confirm the use of the LFA as an applicable screening test, even for patients with cardiovascular disease. In this example, a lateral flow assay (LFA) kit as an immunochromatographic strip was produced for detecting the tM2-PK in a fecal sample. The LFA kit included a gold labeled-monoclonal antibody (gold labeled-mAb) and a polyclonal antibody against the tM2-PK. The monoclonal antibody against the tM2-PK and the polyclonal antibody against the tM2-PK were produced in an exemplary method similar to the method as described in context of EXAMPLE 1.

Firstly, the gold-labeled mAb was produced in two steps including synthesizing gold nanoparticles and coupling the synthesized gold nanoparticles to the monoclonal antibody. In order to synthesize gold nanoparticles, a first solution containing chloroauric acid ($HAuCl_4$) with a concentration of about 0.01% (w/v) was prepared was heated on a stirrer to boil. The first solution was prepared by dissolving the $HAuCl_4$ in deionized and distilled water. Then, a second solution was formed by adding about 20 μl/ml of a sodium citrate solution with a concentration of about 1% w/v to the first solution and stirring on a heater-stirrer at a temperature of about 100° C. until the color changed from light yellow to deep red. After ten (10) minutes of stirring, the reaction was completed and the second solution containing gold nanoparticles was cooled at room temperature and stored at a temperature of about 4° C. until further use.

After that, the pH level of the second solution containing gold nanoparticles was adjusted to about 8.5 using a potassium carbonate ($K_2CO_3$) solution with a concentration of about 0.2 M. In order to couple the gold nanoparticles to the monoclonal antibody against the tM2-PK, the second solution containing the gold nanoparticles were incubated with the monoclonal antibody at a temperature of about 37° C. for a time period of about 1 hour with gentle shaking with a speed of about 80 round per minute (RPM) to form a mixture containing the gold labeled-mAb. Then, the gold labeled-mAb was collected by centrifuging at a speed of about 10000 g and at a temperature of about 4° C. for a time period of about 20 minutes. In the end, the gold labeled mAb was resuspended in a phosphate buffer (PB) solution with a concentration of about 10 mM containing bovine serum albumin (BSA) with a concentration of about 1% w/v and stored at a temperature of about 4° C. until further use.

In the next step, a sample pad (similar to sample pad 202) was formed by immersing a glass fiber pad into a sample pad treatment buffer (pH about 7.2) containing 10 mM phosphate buffer (PB) with about 0.5% w/v bovine serum albumin (BSA), about 0.5% v/v TWEEN 20, and about 5% w/v sucrose for a time period of about 30 minutes at room temperature. The sample pad was dried at a temperature of about 37° C. for a time period of about 3 hours.

Also, a conjugate pad (similar to conjugate pad 204) was formed by immersing a polyester fiber pad into a conjugate pad treatment buffer (pH 7.2) containing 10 mM phosphate buffer (PB) with about 1% w/v BSA, about 0.5% v/v TWEEN 20, about 5% w/v sucrose, and about 0.05% w/v sodium azide for a time period of about 30 minutes at room temperature. The conjugate pad was dried at a temperature of about 37° C. for a time period of about 3 hours. Then, the gold labeled mAb was applied to the conjugate pad and allowed to dry at a temperature of about 37° C. Moreover, Furthermore, a nitrocellulose membrane (similar to nitrocellulose membrane 206) was prepared by coating the polyclonal antibody against tM2-PK in the test zone (T) (similar to test zone 210) for capturing complexes including tM2-PK and gold labeled-mAb during the LFA. Also, a goat anti-mouse antibody was coated in the control zone (C) (similar to control zone 212) for capturing gold labeled-mAb. Then, the nitrocellulose membrane was blocked for a time period of about 15 minutes using a blocking buffer at room temperature and dried at a temperature of about 37° C. for a time period of about 1 hour. The blocking buffer (pH 7.2) contained 10 mM phosphate buffer (PB) with about 1% w/v BSA and about 1% v/v TWEEN 20.

The absorbent pad (similar to absorbent pad 208) included pure plant fibers and was not treated with any buffer. In the end, the LFA kit was produced by attaching all pads and the nitrocellulose membrane on a backing card by an arrangement represented in FIG. 2. The produced LFA kit has a width of about 4 mm and was put into a plastic cassette (similar to cassette 214).

Example 3: Diagnostic Ability of the Lateral Flow Assay Kit for Detecting the Tumor Pyruvate Kinase M2 (tM2-PK) in a Fecal Sample In this example, the diagnostic ability of the LFA kit produced in EXAMPLE 2 for detecting the tM2-PK in a fecal sample was examined. High levels of tM2-PK may be seen in colorectal cancer and precancerous polyps especially greater than 1 cm. The fecal samples were collected from participants before the colonoscopy and delivered to the hospital within 24 hours and immediately frozen until laboratory analysis. The test was performed by a trained person who was blinded to the colonoscopy results.

At first, about 10 mg of each fecal sample was added to a collecting tube and a fecal suspension was formed by adding an extraction buffer to each sample with a ratio of about 5 mg feces/ml extraction buffer. The extraction buffer contained phosphate buffer (PB) with a concentration of about 10 mM at a pH level of about 7.2. Then, the fecal suspensions were completely homogenized by vigorously mixing at room temperature using a vortex. After 10 minutes, the particles of the fecal suspension were settled and the supernatant extract was ready for performing the LFA for detecting the tM2-PK. After that, about 100 µl of the supernatant extract of each fecal sample was added to the sample port of the LFA kit and the test results were visually evaluated after a time period between about 10 minutes and about 15 minutes.

If the tM2-PK protein is present in the fecal samples, the tM2-PK reacts with the gold labeled-mAb and forms (gold-labeled mAb)-(tM2-PK) complexes. This complex then migrates along the nitrocellulose membrane and bind to the polyclonal antibody against the tM2-PK on the test zone which develops a pink-red color line. Also, excess of gold labeled-mAb is trapped by the goat anti-mouse antibody and forms a red control line. Positive tests resulted in two red lines and there is only a control line for negative tests. The absence of the control line means that the LFA is considered invalid and the test should be repeated with another cassette. The cutoff value of tM2-PK was set as 4 U/ml of the fecal suspension.

After that, the sensitivity and the specificity of the LFA kit were calculated by comparing the results of the LFA with the results of colonoscopy as a diagnostic gold standard for detecting CRC. TABLE 1 represents the sensitivity, specificity, a positive predictive value, and a negative predictive value of the LFA kit. Participants detected with CRC or polyps with any size in colonoscopy were considered as patients (positive colonoscopy).

Referring to TABLE. 1, the LFA kit has a sensitivity value of about 86.7%, specificity 91.4%, accuracy 90%, positive predictive value (PPV) 81.3%, and negative predictive value (NPV) of about 94.1%. The sensitivity value has 95% confidence of interval between 62.1 and 96.2. The specificity value has 95% confidence of interval between 77.6 and 97. The accuracy value has 95% confidence of interval between 77.6 and 100. The positive predictive value (PPV) has 95% confidence of interval between 57 and 95. The negative predictive value (NPV) has 95% confidence of interval between 80.1 and 98.9. Also, the sensitivity of the LFA kit for CRC (100%) was significantly higher than the sensitivity for polyps (80%, $p<0.0001$). There was a significant association between the colonoscopy and LFA results ($p<0.0001$).

Figure 4:
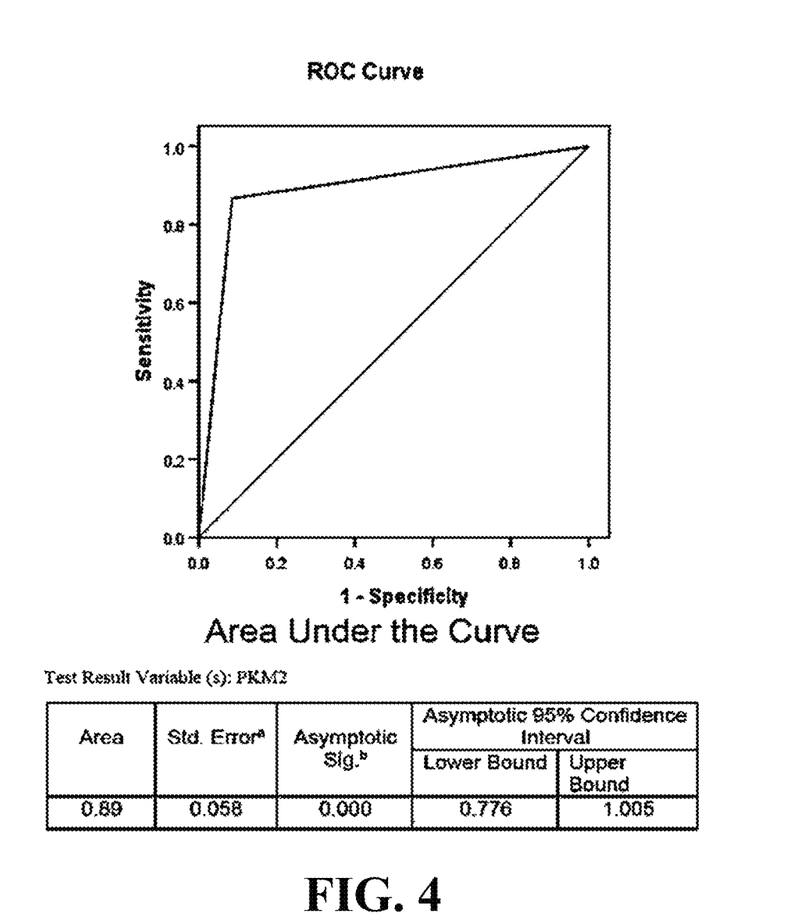
FIG. 4 illustrates a receiver operating characteristic (ROC) curve of a lateral flow assay kit as an exemplary immunoassay kit for detecting tumor pyruvate kinase M2 (tM2-PK) in a fecal sample, consistent with one or more exemplary embodiments of the present disclosure.

Moreover, the receiver operating characteristic (ROC) curve was drawn to visualize the diagnostic ability of the LFA kit. FIG. 4 illustrates a receiver operating characteristic (ROC) curve of the LFA kit as an exemplary immunoassay kit for detecting tumor pyruvate kinase M2 (tM2-PK) in a fecal sample, consistent with one or more exemplary embodiments of the present disclosure. Referring to FIG. 4, the results of the ROC analysis indicated that the overall diagnostic ability of the test was perfect with an area under the curve (AUC) of 0.89. Therefore, the results suggested that the developed LFA detects CRC and precancerous polyps with a relatively high sensitivity value of about 87% and the specificity value of about 91.4%.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in

TABLE 1

Cross-tabulation of results of the tM2-PK test and the colonoscopy

| Cross-tabulation of colonoscopy and tM2-PK test | | | Colonoscopy | | |
| --- | --- | --- | --- | --- | --- |
| | | | Positive | Negative | Total |
| tM2-PK | Positive result | Count | 13 | 3 | 16 |
| | | % within tM2-PK test | 81.3% | 18.8% | 100.0% |
| | | % within colonoscopy | 86.7% | 8.6% | 32.0% |
| | Negative result | Count | 2 | 32 | 34 |
| | | % within tM2-PKtest | 5.9% | 94.1% | 100.0% |
| | | % within colonoscopy | 13.3% | 91.4% | 68.0% |
| | Total | Count | 15 | 35 | 50 |
| | | % within tM2-PK test | 30.0% | 70.0% | 100.0% |
| | | % within colonoscopy | 100.0% | 100.0% | 100.0% | light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such away. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, the inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. An immunoassay kit for detecting tumor pyruvate kinase M2 (tM2-PK) in a biological sample, the immunoassay kit comprising a monoclonal antibody coupled to a labeling agent (a labeled mAb), the monoclonal antibody comprising:
    a heavy chain variable region (HCVR) comprising heavy chain complementarity-determining regions (CDRs), the heavy chain CDRs comprising SEQ ID NOs: 3, 4, and 5; and
    a light chain variable region (LCVR) comprising light chain CDRs, the light chain CDRs comprising SEQ ID NOs: 7, 8, and 9.

2. The immunoassay kit of claim 1 further comprising a polyclonal antibody capable of binding to an epitope within amino acids 433 to 503 of the tM2-PK (SEQ ID NO: 2).

3. The immunoassay kit of claim 1, wherein the HCVR comprises SEQ ID NO: 6.

4. The immunoassay kit of claim 1, wherein the LCVR comprises SEQ ID NO: 10.

5. The immunoassay kit of claim 1, wherein the monoclonal antibody has an isotype of immunoglobulin M (IgM).

6. The immunoassay kit of claim 1, wherein the labeling agent comprises at least one of a luminescent particle, a quantum dot, a chromogen, a catalyst, and a radioactive compound.

7. The immunoassay kit of claim 1 further comprising:
    a conjugate pad comprising the labeled mAb, the monoclonal antibody configured to bind to a first portion of the tM2-PK;
    a nitrocellulose membrane comprising:
        a test zone located downstream of the conjugate pad, the test zone comprising a first immobilized capture reagent, the first immobilized capture reagent configured to bind to a second portion of the tM2-PK, the second portion comprising one or more portions of the tM2-PK other than the first portion; and
        a control zone located downstream of the test zone, the control zone comprising a second immobilized capture reagent, the second immobilized capture reagent configured to bind to the monoclonal antibody; and
    an absorbent pad located downstream of the nitrocellulose membrane, the absorbent pad configured to promote a capillary flow of the biological sample from the conjugate pad toward the control zone.

8. The immunoassay kit of claim 7, wherein the first immobilized capture reagent comprises at least one of a polyclonal antibody, a monoclonal antibody, an antibody fragment, an aptamer.

9. The immunoassay kit of claim 8, wherein the first immobilized capture reagent comprises the polyclonal antibody being capable of binding to an epitope within amino acids 433 to 503 of the tM2-PK (SEQ ID NO: 2).

10. The immunoassay kit of claim 7, wherein the second immobilized capture reagent comprises at least one of an antibody, an antibody fragment, and an aptamer.

11. An immunoassay method for detecting tumor pyruvate kinase M2 (tM2-PK) in a biological sample, comprising:
    contacting the biological sample with a monoclonal antibody coupled to a labeling agent (labeled mAb), the monoclonal antibody comprising:
        a heavy chain variable region (HCVR) comprising heavy chain complementarity-determining regions (CDRs), the heavy chain CDRs comprising SEQ ID NOs: 3, 4, and 5; and
        a light chain variable region (LCVR) comprising light chain CDRs, the light chain CDRs comprising SEQ ID NOs: 7, 8, and 9; and
    detecting the presence of the tM2-PK in the biological sample by detecting the formation of a complex between the tM2-PK and the labeled mAb.

12. The immunoassay method of claim 11, wherein the monoclonal antibody comprises:
    the HCVR (SEQ ID NO: 6); and
    the LCVR (SEQ ID NO: 10).

13. The immunoassay method of claim 11, wherein detecting the presence of the tM2-PK in the biological sample comprises detecting the presence of the tM2-PK in the biological sample with a cutoff value of 4 U/ml of the tM2-PK in the biological sample.

14. The immunoassay method of claim 11, wherein the labeling agent comprises at least one of a luminescent particle, a quantum dot, a chromogen, a catalyst, and a radioactive compound.

15. The immunoassay method of claim 11, wherein detecting the presence of the tM2-PK in the biological sample comprises detecting the presence of the tM2-PK in the biological sample by conducting at least one of a chemiluminescent assay, an immunofluorescent assay, enzyme-linked immunosorbent assay (ELISA), radioimmunoassay, a Western blot assay, an enzyme immunoassay, an immunoprecipitation assay, an immunohistochemical assay, an immunochromatographic assay, a dot blot assay, a slot blot assay.

16. The immunoassay method of claim 15, wherein detecting the presence of the tM2-PK in the biological sample comprises detecting the presence of the tM2-PK in the biological sample by conducting a lateral flow assay (LFA).

17. The immunoassay method of claim 16, wherein conducting the lateral flow assay (LFA) comprises providing a lateral flow assay (LFA) kit, the LFA kit comprising:
- a conjugate pad comprising the monoclonal antibody coupled to the labeling agent (the labeled mAb), the monoclonal antibody configured to bind to a first portion of the tM2-PK;
- a nitrocellulose membrane comprising:
  - a test zone located downstream of the conjugate pad, the test zone comprising a first immobilized capture reagent, the first immobilized capture reagent configured to bind to a second portion of the tM2-PK, the second portion comprising one or more portions of the tM2-PK other than the first portion of the tM2-PK; and
  - a control zone located downstream of the test zone, the control zone comprising a second immobilized capture reagent, the second immobilized capture reagent configured to bind to the monoclonal antibody; and
- an absorbent pad located downstream of the nitrocellulose membrane, the absorbent pad configured to promote a capillary flow of the biological sample from the conjugate pad toward the control zone.

18. The immunoassay method of claim 17, wherein the first immobilized capture reagent comprises at least one of a polyclonal antibody, a monoclonal antibody, an antibody fragment, an aptamer.

19. The immunoassay method of claim 18, wherein the first immobilized capture reagent comprises the polyclonal antibody being capable of binding to an epitope within amino acids 433 to 503 of the tM2-PK (SEQ ID NO: 2).

20. The immunoassay method of claim 17, wherein the second immobilized capture reagent comprises at least one of an antibody, an antibody fragment, an aptamer.

* * * * *

SEQUENCE LISTING

```
<160> NUMBER OF SEQ ID NOS: 11

<210> SEQ ID NO 1
<211> LENGTH: 36
<212> TYPE: PRT
<213> ORGANISM: Homo sapiens

<400> SEQUENCE: 1

Gln Leu Phe Glu Glu Leu Arg Arg Leu Ala Pro Ile Thr Ser Asp Pro
1               5                   10                  15

Thr Glu Ala Thr Ala Val Gly Ala Val Glu Ala Ser Phe Lys Cys Cys
            20                  25                  30

Ser Gly Ala Ile
        35

<210> SEQ ID NO 2
<211> LENGTH: 71
<212> TYPE: PRT
<213> ORGANISM: Homo sapiens

<400> SEQUENCE: 2

Lys Ser Gly Arg Ser Ala His Gln Val Ala Arg Tyr Arg Pro Arg Ala
1               5                   10                  15

Pro Ile Ile Ala Val Thr Arg Asn Pro Gln Thr Ala Arg Gln Ala His
            20                  25                  30

Leu Tyr Arg Gly Ile Phe Pro Val Leu Cys Lys Asp Pro Val Gln Glu
        35                  40                  45

Ala Trp Ala Glu Asp Val Asp Leu Arg Val Asn Phe Ala Met Asn Val
    50                  55                  60
```

```
Gly Lys Ala Arg Gly Phe Phe
 65                  70

<210> SEQ ID NO 3
<211> LENGTH: 10
<212> TYPE: PRT
<213> ORGANISM: Artificial Sequence
<220> FEATURE:
<223> OTHER INFORMATION: Synthetic sequence

<400> SEQUENCE: 3

Gly Tyr Asn Ile Thr Gly Thr Tyr Met Asn
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic sequence

<400> SEQUENCE: 4

Arg Ile Asp Pro Ala Asn Gly Asp Ser Leu Tyr Asp Gln Lys Phe Gln
1               5                   10                  15

Gly

<210> SEQ ID NO 5
<211> LENGTH: 6
<212> TYPE: PRT
<213> ORGANISM: Artificial Sequence
<220> FEATURE:
<223> OTHER INFORMATION: Synthetic sequence

<400> SEQUENCE: 5

Asp Tyr Gly Gly His Asn
1               5

<210> SEQ ID NO 6
<211> LENGTH: 118
<212> TYPE: PRT
<213> ORGANISM: Artificial Sequence
<220> FEATURE:
<223> OTHER INFORMATION: Synthetic sequence

<400> SEQUENCE: 6

Glu Val Gln Leu Gln Gln Ser Gly Pro Glu Leu Val Lys Pro Gly Ala
1               5                   10                  15

Ser Val Lys Leu Ser Cys Thr Ala Ser Gly Tyr Asn Ile Thr Gly Thr
            20                  25                  30

Tyr Met Asn Trp Val Lys Gln Arg Pro Glu Lys Ser Leu Glu Trp Ile
        35                  40                  45

Gly Arg Ile Asp Pro Ala Asn Gly Asp Ser Leu Tyr Asp Gln Lys Phe
    50                  55                  60

Gln Gly Lys Ala Thr Ile Thr Ala Asp Lys Ser Ser Thr Thr Ala Tyr
65                  70                  75                  80

Leu Gln Leu Ser Ser Leu Thr Ser Glu Asp Ser Ala Val Tyr Tyr Cys
                85                  90                  95

Ala Phe Asp Tyr Gly Gly His Asn Trp Gly Gln Gly Thr Thr Leu Val
            100                 105                 110

Thr Val Ser Ala Glu Ser
        115
```

<210> SEQ ID NO 7
<211> LENGTH: 16
<212> TYPE: PRT
<213> ORGANISM: Artificial Sequence
<220> FEATURE:
<223> OTHER INFORMATION: Synthetic sequence

<400> SEQUENCE: 7

Lys Ser Ser Gln Ser Leu Val Tyr Ser Asn Gly Lys Thr Tyr Leu Asn
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Synthetic sequence

<400> SEQUENCE: 8

Leu Ala Ser Asn Leu Glu Ser
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic sequence

<400> SEQUENCE: 9

Val Gln Ser Tyr Thr His Val Pro
1               5

<210> SEQ ID NO 10
<211> LENGTH: 111
<212> TYPE: PRT
<213> ORGANISM: Artificial Sequence
<220> FEATURE:
<223> OTHER INFORMATION: Synthetic sequence

<400> SEQUENCE: 10

Asp Val Val Leu Thr Gln Thr Pro Leu Ser Leu Pro Val Ser Leu Gly
1               5                   10                  15

Gln Pro Ala Ser Ile Ser Cys Lys Ser Ser Gln Ser Leu Val Tyr Ser
            20                  25                  30

Asn Gly Lys Thr Tyr Leu Asn Trp Leu Gln Gln Arg Pro Gly Gln Ser
        35                  40                  45

Pro Lys Leu Leu Val Tyr Leu Ala Ser Asn Leu Glu Ser Gly Val Pro
    50                  55                  60

Asp Arg Phe Ser Gly Ser Arg Ser Gly Thr Asp Tyr Thr Leu Lys Ile
65                  70                  75                  80

Ser Arg Val Glu Ser Glu Asp Leu Gly Val Tyr Tyr Cys Val Gln Ser
                85                  90                  95

Tyr Thr His Val Pro Phe Gly Ser Gly Thr Lys Leu Glu Ile Lys
            100                 105                 110

<210> SEQ ID NO 11
<211> LENGTH: 531
<212> TYPE: PRT
<213> ORGANISM: Homo sapiens

<400> SEQUENCE: 11

Met Ser Lys Pro His Ser Glu Ala Gly Thr Ala Phe Ile Gln Thr Gln

-continued

```
1               5                   10                  15
Gln Leu His Ala Ala Met Ala Asp Thr Phe Leu Glu His Met Cys Arg
            20                  25                  30
Leu Asp Ile Asp Ser Pro Pro Ile Thr Ala Arg Asn Thr Gly Ile Ile
            35                  40                  45
Cys Thr Ile Gly Pro Ala Ser Arg Ser Val Glu Thr Leu Lys Glu Met
            50                  55                  60
Ile Lys Ser Gly Met Asn Val Ala Arg Leu Asn Phe Ser His Gly Thr
65                  70                  75                  80
His Glu Tyr His Ala Glu Thr Ile Lys Asn Val Arg Thr Ala Thr Glu
            85                  90                  95
Ser Phe Ala Ser Asp Pro Ile Leu Tyr Arg Pro Val Ala Val Ala Leu
            100                 105                 110
Asp Thr Lys Gly Pro Glu Ile Arg Thr Gly Leu Ile Lys Gly Ser Gly
            115                 120                 125
Thr Ala Glu Val Glu Leu Lys Lys Gly Ala Thr Leu Lys Ile Thr Leu
            130                 135                 140
Asp Asn Ala Tyr Met Glu Lys Cys Asp Glu Asn Ile Leu Trp Leu Asp
145                 150                 155                 160
Tyr Lys Asn Ile Cys Lys Val Val Glu Val Gly Ser Lys Ile Tyr Val
            165                 170                 175
Asp Asp Gly Leu Ile Ser Leu Gln Val Lys Gln Lys Gly Ala Asp Phe
            180                 185                 190
Leu Val Thr Glu Val Glu Asn Gly Gly Ser Leu Gly Ser Lys Lys Gly
            195                 200                 205
Val Asn Leu Pro Gly Ala Ala Val Asp Leu Pro Ala Val Ser Glu Lys
            210                 215                 220
Asp Ile Gln Asp Leu Lys Phe Gly Val Glu Gln Asp Val Asp Met Val
225                 230                 235                 240
Phe Ala Ser Phe Ile Arg Lys Ala Ser Asp Val His Glu Val Arg Lys
            245                 250                 255
Val Leu Gly Glu Lys Gly Lys Asn Ile Lys Ile Ile Ser Lys Ile Glu
            260                 265                 270
Asn His Glu Gly Val Arg Arg Phe Asp Glu Ile Leu Glu Ala Ser Asp
            275                 280                 285
Gly Ile Met Val Ala Arg Gly Asp Leu Gly Ile Glu Ile Pro Ala Glu
            290                 295                 300
Lys Val Phe Leu Ala Gln Lys Met Met Ile Gly Arg Cys Asn Arg Ala
305                 310                 315                 320
Gly Lys Pro Val Ile Cys Ala Thr Gln Met Leu Glu Ser Met Ile Lys
            325                 330                 335
Lys Pro Arg Pro Thr Arg Ala Glu Gly Ser Asp Val Ala Asn Ala Val
            340                 345                 350
Leu Asp Gly Ala Asp Cys Ile Met Leu Ser Gly Glu Thr Ala Lys Gly
            355                 360                 365
Asp Tyr Pro Leu Glu Ala Val Arg Met Gln His Leu Ile Ala Arg Glu
            370                 375                 380
Ala Glu Ala Ala Ile Tyr His Leu Gln Leu Phe Glu Glu Leu Arg Arg
385                 390                 395                 400
Leu Ala Pro Ile Thr Ser Asp Pro Thr Glu Ala Thr Ala Val Gly Ala
            405                 410                 415
Val Glu Ala Ser Phe Lys Cys Cys Ser Gly Ala Ile Ile Val Leu Thr
            420                 425                 430
```

```
Lys Ser Gly Arg Ser Ala His Gln Val Ala Arg Tyr Arg Pro Arg Ala
        435             440             445
Pro Ile Ile Ala Val Thr Arg Asn Pro Gln Thr Ala Arg Gln Ala His
    450             455             460
Leu Tyr Arg Gly Ile Phe Pro Val Leu Cys Lys Asp Pro Val Gln Glu
465             470             475             480
Ala Trp Ala Glu Asp Val Asp Leu Arg Val Asn Phe Ala Met Asn Val
            485             490             495
Gly Lys Ala Arg Gly Phe Phe Lys Lys Gly Asp Val Val Ile Val Leu
            500             505             510
Thr Gly Trp Arg Pro Gly Ser Gly Phe Thr Asn Thr Met Arg Val Val
        515             520             525
Pro Val Pro
    530
```